United States Patent [19]
Lanier et al.

[11] 3,960,689
[45] June 1, 1976

[54] pH REFERENCE ELECTRODE

[75] Inventors: Terry O. Lanier, Northboro; Nunna Ramanaiah, Framingham, both of Mass.

[73] Assignee: Corning Glass Works, Corning, N.Y.

[22] Filed: Jan. 28, 1974

[21] Appl. No.: 437,170

[52] U.S. Cl.............................. 204/195 F; 324/30 R
[51] Int. Cl.² ................... G01N 27/56; G01N 27/30
[58] Field of Search............ 204/1 T, 195 F, 195 R

[56] References Cited
UNITED STATES PATENTS

| | | | |
|---|---|---|---|
| 2,760,922 | 8/1956 | Williams | 204/195 R |
| 3,455,793 | 7/1969 | Watanabe et al. | 204/195 F |
| 3,676,319 | 7/1972 | Kirsten | 204/195 F |

FOREIGN PATENTS OR APPLICATIONS

| | | | |
|---|---|---|---|
| 39-27217 | 11/1964 | Japan | 204/195 F |
| 678,648 | 9/1952 | United Kingdom | 204/195 F |
| 729,575 | 5/1955 | United Kingdom | 204/195 F |

*Primary Examiner*—T. Tung
*Attorney, Agent, or Firm*—James A. Giblin; Clinton S. Janes, Jr.; Clarence R. Patty, Jr.

[57] ABSTRACT

A relatively constant concentration of the electrolytic salt bridge solution within a pH reference electrode is maintained by including crystals of the electrolyte salt in a concentrated but not saturated solution. In a preferred electrode, the electrolytic salt bridge is a concentrated KCl solution (e.g. about 4 M/l) within which KCl crystals are held in place by an inert foraminous material disposed intermediate an internal reference electrode and a passageway in the electrode housing through which is established electrochemical contact between the salt bridge and a fluid, the pH of which is to be measured.

5 Claims, No Drawings pH REFERENCE ELECTRODE

BACKGROUND OF THE INVENTION

1. Field

This invention relates generally to pH reference electrodes and specifically to such electrodes which have a liquid electrolytic salt bridge which provides electrical continuity between an internal reference electrode and a fluid, the pH of which is to be determined.

2. Prior Art

The hydrogen ion concentration of a fluid is commonly determined with a pH electrode and a pH reference electrode. Each electrode has a lead in electrical contact with appropriate terminals of an electrometer and, in use, both electrodes are brought into electrical contact with a fluid, the pH of which is to be determined, and an electrical circuit is completed. The pH reference electrode provides a stable and accurate voltage against which the output of the pH electrode, as varied by hydrogen ion activity, may be measured. The construction of the pH electrode is such that it "senses" hydrogen ion activity in the fluid and, ultimately, relates that activity to hydrogen ion concentration which is readily expressable in pH units by the electrometer.

Various configurations for pH reference electrodes are well known. The essential features of such electrodes are an internal reference electrode having a lead connectable to an electrometer and an electrical "bridge" which provides electrical continuity between the internal reference electrode and a fluid, the pH of which is to be measured. A very common bridge consists of a salt solution, often saturated. Such a solution can be found in so-called saturated Calomel Reference Electrodes (S.C.E.). Operability of a pH reference electrode having a liquid electrolytic salt bridge requires that the salt bridge solution be readily accessable to the fluid with which the pH reference electrode is contacted. This is readily accomplished by containing the electrolyte in an electrode housing which has a small orifice through which electrical continuity is established. See, for example, U.S. Pat. No. 3,505,196. Such an orifice is often covered with a semi-permeable membrane (e.g. cellophane) which helps keep materials such as proteins from plugging the orifice.

The use of a "saturated" solution as an electrolytic salt bridge assures a constant concentration of the salt bridge and, hence, reliable pH determinations, especially for precious fluids such as blood for which precise pH determinations are often required. In using electrodes having a saturated salt solution as the electrolytic salt bridge, it is a common practice to include crystals of the salt within the saturated solution to assure prolonged saturation with repeated use of the electrode. Unfortunately, however, the use of a saturated salt bridge solution, either with or without added salt crystals, often results in the formation of additional salt crystals within the solution which can block the orifice through which electrical continuity is maintained. Because of such undesirable crystal formation, it is sometimes necessary, prior to using the electrode, to immerse it in warm water to dissolve crystals which may be blocking the orifice. Although the above step has been commonly accepted as a necessary inconvenience associated with using saturated salt bridge solutions, there have been developed various techniques and pH reference elctrodes which tend to avoid the problems associated with using saturated solutions.

For example, in Canadian Pat. No. 878,722, there is disclosed a reference electrode which does away with the need for a saturated solution by incorporating KCl crystals within a polymeric matrix which is in electrical contact with an internal reference electrode. Further, in an article by A. J. Maas, Clinica Chemica Acta, 28, 373–390 (1970) it has been suggested that reliable pH measurements of body fluids (e.g. blood) can be made by using an isotonic NaCl solution as the salt bridge (e.g. 0.16 moles/liter NaCl). See also the description of the preferred pH reference electrode in U.S. Pat. No. 3,763,422, incorporated herein by reference. Another method of avoiding problems associated with the formation of undesired crystals within a pH reference electrode involves immersing a "flow-through" pH electrode (e.g. U.S. Pat. No. 3,357,910) containing a blood sample and a pH reference electrode in an open beaker containing a saturated KCl solution and then reading the measured pH of the sample within the flow-through pH electrode. For examples of such a system see a catalogue (SI-20) entitled, "Scientific Instruments", dated March, 1973 and published by Corning Glass Works, Scientific Instruments, Medfield, Massachusetts 02052.

In using an open beaker containing a saturated KCl solution, a constant salt bridge concentration, and, hence, a reliable pH measurement is assured. However, it has been recognized that the use of such an open beaker results in so-called "KCl creep" which involves the growth of KCl crystals up the sides of the beaker and this results in an unsightly mess which should be cleaned frequently to avoid damage to laboratory equipment and/or instruments. A novel method for avoiding KCl creep is disclosed in U.S. patent application Ser. No. 408,301 filed on Oct. 23, 1973, entitled "Electrolyte Container for pH Measurements", assigned to the present assignee, and incorporated herein by reference. In the above-entitled patent application, it is disclosed that KCl creep can be avoided by maintaining the saturated KCl solution in an essentially air-tight container into which both a flow-through pH electrode and a pH reference electrode can be inserted.

Although the above disclosures suggest various ways for assuring reliable pH measurements when various salt bridges are used, it is significant that the above methods of electrodes, in one way or another, avoid the problems associated with saturated electrolytic salt solutions by not using a liquid bridge (Canadian Pat. No. 1,274,349), using separate containers for the saturated solution (e.g. U.S. Ser. No. 408,301), or requiring the use of isotonic salt solutions (e.g. A. J. Maas, above on the preferred pH reference electrode of U.S. Pat. No. 3,763,422). Quite surprisingly, we have now found that the problems associated with saturated solutions need no longer be avoided by the rather elaborate techniques already devised. Rather than provide another elaborate method for avoiding the problem, we have surprisingly solved it with the novel pH reference electrode described in detail below.

SUMMARY OF THE INVENTION

Our pH reference electrode comprises, in combination, an electrode housing containing a concentrated but less than saturated electrolytic salt solution and crystals of the salt, an internal reference electrode in electrical contact with the solution, and means in the electrode housing defining a passageway for electrical continuity betwen the electrolytic salt solution and a fluid, the ph of which is to be determined. In a preferred pH reference electrode, the concentrated electrolytic salt solution has a concentration of about 4 moles of KCl per liter of water and the crystals are KCl crystals retained within the solution by an inert foraminous material disposed intermediate the internal reference electrode and the passageway through which electrochemical contact between the electrolyte and the fluid is established.

SPECIFIC EMBODIMENTS OF THE INVENTION

One relatively simple method of avoiding the problems associated with saturated solutions involves using a concentrated, but less than saturated, solution. For example a saturated KCl solution consists of about 4.2 moles KCl per liter of water. By using a concentrated, but less than saturated solution (e.g. about 4.0 moles/liter) within a pH reference electrode, we have found that the problems of crystal formation within the electrode are virtually eliminated. As used herein, the term "concentrated" when applied to salt bridge solutions, refers to such solutions containing a substantial amount of dissolved salt, but not enough to form a true saturated system. For a concentrated KCl solution, this amounts to about 4.0 moles KCl per liter.

In using pH reference electrodes having such a concentrated salt bridge, it has been found that, with repeated use, the concentration of the salt decreases fairly rapidly due to salt depletion from the concentrated solution to the fluid being measured. To obtain reliable pH measurements, especially in precious fluids such as blood in which pH measurements must be precise, the concentration of the electrolytic salt bridge in the pH reference electrode should be maintained constant. Hence, to assure precision in blood pH measurement it is now a common practice to replenish the concentrated electrolytic salt bridge on a daily basis by simply removing the spent electrolyte and replacing it with a fresh concentrated solution (e.g. 4 M/l KCl solution). Such daily replenishments not only add to maintenance requirements for a blood pH measurement system, but, because of their frequency, they increase the likelihood of damage to the delicate semipermeable membrane and/or the electrode itself. Although the above described maintenance operation has come to be accepted as an unavoidable inconvenience in using such a pH reference electrode having a concentrated salt bridge, we have found that the maintenance procedure can be avoided by including salt crystals within the less than saturated, but concentrated, solution.

A very critical feature of our pH reference electrode is the inclusion of salt crystals within the concentrated salt solution which forms the electrolytic bridge. As pointed out above, it had been common practice in the past to replenish the solution daily to assure a constant concentration required for reliable pH determinations, especially in blood, where determinations are regularly made in thousandths of a pH unit and within a pH unit range of only one unit (e.g. about 7,000 to 8,000, the commonly accepted "normal" value of blood being about pH 7.35 to 7.47). As discussed below, blood pH determinations vary as the electrolytic salt concentration varies. Hence, assurance of a constant electrolytic concentration assures a reliable pH determination.

Figure 1:
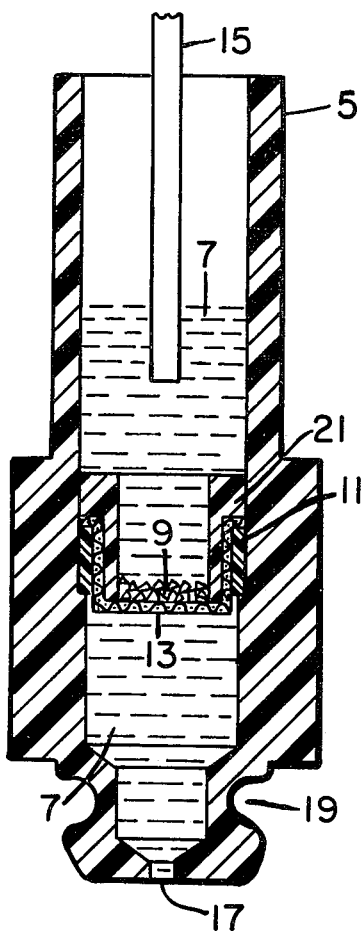
FIG. 1 is a cross sectional illustration showing the construction of our preferred pH reference electrode.

The actual construction of a preferred electrode of the present invention can be seen in FIG. 1 which is a cross-sectional illustration of one embodiment of our pH reference electrode. That electrode consists of an electrode housing 5 made from a conventional electrode housing material (e.g. polymeric tetrafluoroethylene) which contains a concentrated KCl electrolytic salt solution 7. Immersed in, and in electrical contact with, the solution 7 is an internal reference electrode 15 shown very generally in FIG. 1. The internal reference electrode 15 serves to provide electrical continuity between the solution 7 and an electrometer (pH meter) not shown. Electrical contact between the solution 7 and a fluid, the pH of which is to be determined, occurs through a small aperture 17 (about 1 mm diameter). In pH reference electrodes which come in contact with blood or other body fluids, it is a common practice to place a semi-permeable dialysis membrane (e.g. cellophane) over an aperture such as 17 to prevent substances such as proteins from plugging the aperture. Such a membrane (not shown) consists of a thin piece of dialysis material which is simply wrapped flatly over the lower end of the electrode (see FIG. 1) and held in place by an elastic O-ring which holds edges of the membrane tightly against a recess 19 adapted to receive the O-ring. The use of an elastic O-ring and the type of recess 19 shown generally in FIG. 1 permits easy membrane exchange.

Disposed intermediate the internal reference electrode 15 and the aperture 17, is an inert foraminous material 13 having openings smaller than the crystals 9 held thereon. In our preferred electrode, the foraminous material 13 consisted of a screen of about 10 to 12 mesh, U.S. Standard Sieve, which was made from polymeric fluorinated hydrocarbon fibers. Such as screening material is sold under the name Fluortex. It should be pointed out, however, that other inert foraminous materials can be used as crystal retainers (e.g. nylon, ect.). It is only essential that the material be relatively inert to the concentrated salt solution. Further, the aperture size (e.g. mesh size) can vary, depending on crystal size. In the preferred electrode illustrated in FIG. 1, the salt solution 7 consisted of an aqueous concentrated KCl solution (e.g. 4.0 moles KCl per liter) and the actual amount of the solution was about 0.80 ml. The crystals were KCl crystals (about 2 mg crystals of analytical reagent grade KCl crystals) having an average particle size of about 50 to 60 mesh. The foraminous material 13 was held in place by counter boring the inside of a conventional pH reference electrode housing (e.g. Corning Stock No. 298700) to form a circular shoulder 11 against which a circular plastic stopper 21 having a central opening was held in place frictionally with the outer edges of the foraminous material pressed between the shoulder 11 and the open stopper 21. Other means of retaining the crystals between the aperture 17 and the internal reference electrode 15 are possible. The main purpose of suspending the crystals on such a material is to avoid the possibility of crystals plugging the aperture 17. Hence, we have found that the openings in the foraminous material (e.g. mesh size) should preferably be smaller than the aperture 17 so that the passageway will not be obstructed.

The above described pH reference electrode was used successfully for an extended period of time as the pH reference electrode in a commercial blood gas analyzer (Corning Model 165 Blood Gas Analyzer) and found to have several advantages over a similar pH reference electrode which contained a concentrated KCl solution but no KCl crystals. A general description of the aboveidentified blood gas analyzer can be found in U.S. Pat. No. 3,736,422.

Figure 2:
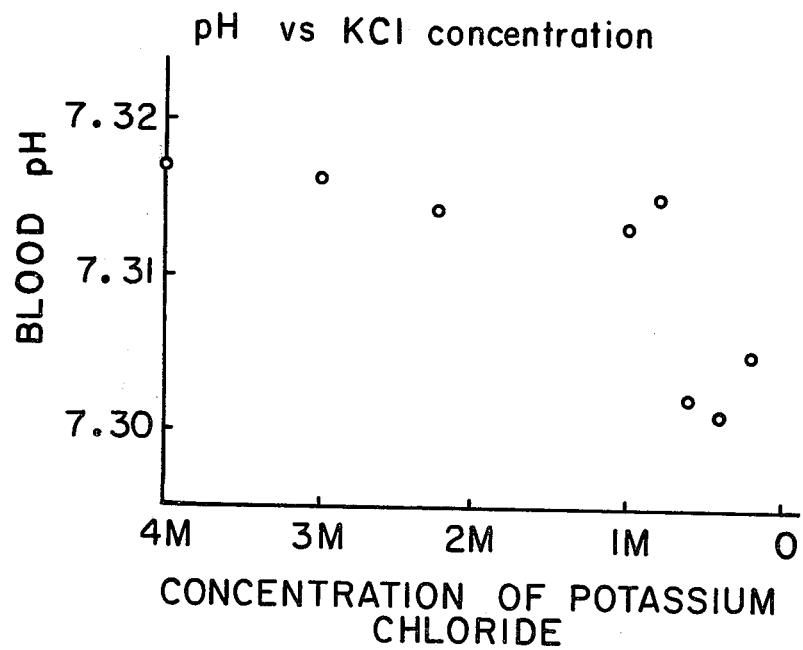
FIG. 2 is a graph illustrating the effect of KCl concentration changes in a prior art pH reference electrode on blood pH measurements.

FIG. 2 graphically shows the effect of diminishing KCl concentration on blood pH determinations. As can be seen in FIG. 2, there appears an apparent decrease in blood pH as the molarity of the KCl decreases, thus affecting pH reliability with repetitive use of the pH reference electrode. As pointed out above, to assure pH reliability, it is common practice to replenish the concentrated KCl solution daily to assure a fairly constant concentration. However, by following the teachings of this disclosure (e.g. adding KCl crystals to the concentrated KCl solution) such concentration can be maintained for at least two weeks using commercially available KCl crystals on a retainer screen of about 10–12 mesh.

Figure 3:
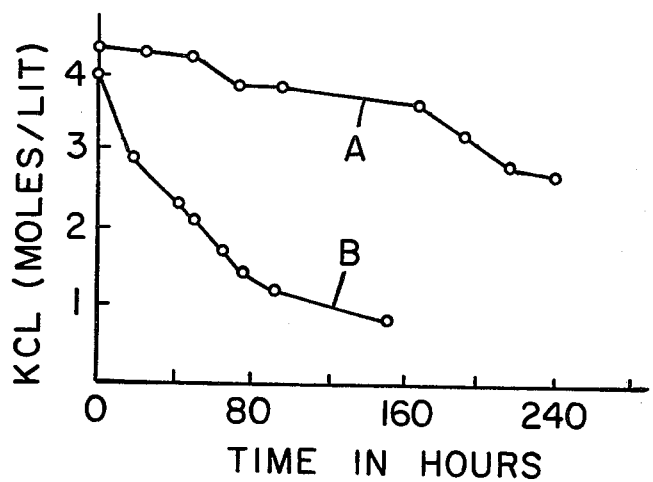
FIG. 3 is a graph comparing the decreases in concentration of KCl with time in both a prior art electrode (B) and a preferred electrode of the present invention (A).

FIG. 3 graphically compares the change in concentration with time of an initially 4.0 molar KCl solution (see B of FIG. 3) with the same solution initially containing KCl crystals (about 2 mg KCl crystals per ml of saturated KCl solution—see A of FIG. 3).

The preferred electrode of this disclosure was compared with commercially available pH reference electrode (Model E 5021, Radiometer Corp.) on 30 clinical blood samples over a period of 1 week. The results were plotted on a regression plot with excellent correlation.

Although the above-disclosed pH reference electrode is particularly suitable for maintaining a constant concentration of saturated KCl solution, the teachings of this disclosure can also be applied to other concentrated, but not saturated, solutions (e.g. NaCl crystals to maintain a concentrated NaCl solution). For example, as the concentration of any concentrated salt solution tends to change (lessen) at the bottom of the electrode due to dialysis through a semi-permeable membrane, the more concentrated salt solution near the salt crystals will tend to move down due to the concentration gradient, thus maintaining a relatively constant saturated salt concentration.

The preferred pH reference electrode (containing KCl crystals in a 4.0 molar KCl solution) was used for a prolonged period of time in the blood-gas analysis system disclosed in U.S. Pat. No. 3,763,422, and there was no adverse effect on the response or accuracy of the pH measuring system. It was also found that an improvement in calibration stability was experienced. Greater stability in buffer readings and less time drift in calibration accompanied the use of the electrode containing the KCl crystals.

Given the above disclosure, it is anticipated that numerous variations of the preferred electrode will become apparent to those skilled in the art. Accordingly, it is intended that the above descriptions should be construed as illustrative only and that the scope of the present invention should be limited only by the appended claims.

We claim:

1. In a pH reference electrode comprising an electrode housing containing a concentrated KCl solution, an internal reference electrode in electrical contact with the solution, and means in the electrode housing defining a passageway for electrochemical contact between the solution and a fluid, the pH of which is to be determined, the improvement which comprises providing KCl crystals in the solution, the crystals being held in place by an inert foraminous material disposed intermediate the internal reference electrode and the passageway and the foraminous material being a screen having orifaces smaller than the passageway.

2. The electrode of claim 1 wherein the KCl solution consists of about a 4.0 molar KCl solution.

3. The electrode of claim 1 wherein the screen consists of fibers of a fluorinated hydrocarbon material having a mesh size of about 10 to 12 mesh, U.S. Standard Sieve.

4. The electrode of claim 1 wherein the passageway is covered by a semipermeable membrane.

5. The electrode of claim 1 wherein the membrane consists of cellophane.

* * * * *